US012765552B2

(12) United States Patent
Ke et al.

(10) Patent No.: US 12,765,552 B2
(45) Date of Patent: Oct. 20, 2026

(54) POLYSUBSTITUTED NITROGEN-CONTAINING HETEROCYCLIC DERIVATIVES, PREPARATION METHOD AND USE THEREOF

(71) Applicant: Hubei Biopesticide Engineering Research Centre, Wuhan (CN)

(72) Inventors: Shaoyong Ke, Wuhan (CN); Hongtao Hu, Wuhan (CN); Ronghua Zhou, Wuhan (CN); Zhigang Zhang, Wuhan (CN); Fang Liu, Wuhan (CN); Shaohua Wen, Wuhan (CN); Zhaoyuan Wu, Wuhan (CN); Yani Zhang, Wuhan (CN); Wei Fang, Wuhan (CN); Kui Li, Wuhan (CN); Xiaoyu Li, Wuhan (CN); Kaimei Wang, Wuhan (CN); Yan Gong, Wuhan (CN); Jingzhong Yang, Wuhan (CN)

(73) Assignee: Hubei Biopesticide Engineering Research Centre, Hubei (CN)

( * ) Notice: Subject to any disclaimer, the term of this patent is extended or adjusted under 35 U.S.C. 154(b) by 392 days.

(21) Appl. No.: 18/368,514

(22) Filed: Sep. 14, 2023

(65) Prior Publication Data

US 2024/0215578 A1 Jul. 4, 2024

(30) Foreign Application Priority Data

Dec. 13, 2022 (CN) ........................ 202211606984.9

(51) Int. Cl.
*A01N 43/42* (2006.01)
*A01N 43/60* (2006.01)
(Continued)

(52) U.S. Cl.
CPC ............ *A01N 43/42* (2013.01); *A01N 43/60* (2013.01); *A01N 43/90* (2013.01); *A01P 1/00* (2021.08);
(Continued)

(58) Field of Classification Search
CPC ........ A01N 43/42; A01N 43/60; A01N 43/90; A01P 1/00
See application file for complete search history.

(56) References Cited

U.S. PATENT DOCUMENTS 4,663,457 A * 5/1987 Mich .................. C07D 213/74
546/156

FOREIGN PATENT DOCUMENTS

CN 110256480 A 9/2019
CN 113061137 A 7/2021
(Continued)

OTHER PUBLICATIONS

English translation of WO2017/113268, Google patents (Year: 2017).*

*Primary Examiner* — San Ming R Hui
(74) *Attorney, Agent, or Firm* — George D. Morgan

(57) ABSTRACT

The present invention provides a polysubstituted nitrogen-containing heterocyclic derivative, a preparation method, and use thereof. In the present invention, the novel structure of the natural nitrogen-containing heterocyclic molecule is designed to obtain the polysubstituted nitrogen-containing heterocyclic derivative. The polysubstituted nitrogen-containing heterocyclic derivatives have obvious bactericidal activity, and some compounds have significant bactericidal activity against diseases such as *E. carotovora, E. coli,* and *R. solanacearum,* which can be widely applied in the comprehensive prevention and control of agricultural and forestry bacterial diseases. The bactericide obtained by
(Continued)

mixing the polysubstituted nitrogen-containing heterocyclic derivative of the present invention with various adjuvants also have good bactericidal effects on *E. coli, E. carotovora, R. solanacearum,* etc.

1 Claim, 4 Drawing Sheets

(51) Int. Cl.

| | |
|---|---|
| ***A01N 43/90*** | (2006.01) |
| ***A01P 1/00*** | (2006.01) |
| ***C07D 215/233*** | (2006.01) |
| ***C07D 215/36*** | (2006.01) |
| ***C07D 215/56*** | (2006.01) |
| ***C07D 471/04*** | (2006.01) |

(52) U.S. Cl.
CPC ....... *C07D 215/233* (2013.01); *C07D 215/36* (2013.01); *C07D 215/56* (2013.01); *C07D 471/04* (2013.01)

(56) References Cited

FOREIGN PATENT DOCUMENTS

| | | | | |
|---|---|---|---|---|
| CN | 113683630 | A | 11/2021 | |
| WO | WO-2017113268 | A1 * | 7/2017 | ......... A61K 31/4375 |

* cited by examiner

POLYSUBSTITUTED NITROGEN-CONTAINING HETEROCYCLIC DERIVATIVES, PREPARATION METHOD AND USE THEREOF

CROSS-REFERENCE TO RELATED APPLICATIONS

The application claims priority to Chinese patent application No. 202211606984.9, filed on Dec. 13, 2022, the entire contents of which are incorporated herein by reference.

TECHNICAL FIELD

The present invention relates to the technical field of biopharmaceuticals, and in particular to polysubstituted nitrogen-containing heterocyclic derivatives, a preparation method, and use thereof.

BACKGROUND

Plant bacterial diseases usually refer to plant diseases caused by a series of physiological lesions of cells and tissues, such as soft rot, black rot, canker, bacterial wilt, leaf blight, spot disease, and so on. In recent years, bacterial diseases have become the second most common disease in agricultural production in China, second only to fungal diseases. They occur in vegetables, fruit trees, rice, or various other crops, and multiple bacterial diseases can occur on the same plant species. Bacterial diseases often spread in a variety of ways, characterized by outbreaks, epidemics, and destructiveness, making prevention and control increasingly difficult. For example, bacterial wilt is a bacterial soil-borne disease widely distributed around the world. Soil acidification and hardening can cause bacterial wilt to occur in a large area, and in the middle and late stages of the disease, treatment is exceptionally difficult. Bacterial wilt can infect 200 kinds of crops in up to 50 families. It can cause tomato, pepper, ginger, tobacco, and other crops to die, reduce yield, and even destroy the plantation. Bacterial wilt can cause great loss of potato yield every year.

Common crop bacterial diseases include soft rot, ulcer, bacterial wilt, rice bacterial leaf blight, rice bacterial leaf streak, soybean bacterial blight, and black rot. The bacterial wilt of solanaceous plants, such as capsicum, tomato, and tobacco, is a devastating vascular disease, which can cause a reduction of 20-50% in production. At present, there are very few kinds and quantities of pesticides to control bacterial diseases in China, and most of them are copper products and antibiotics. After long-term use, the resistance of pathogens is increasingly serious, and the control effect of existing pesticides is decreasing.

Based on the limited number of pesticides used to prevent and control bacterial diseases and the existing problems, it is necessary to make improvements in this regard.

SUMMARY

In view of the above, the present invention proposes a polysubstituted nitrogen-containing heterocyclic derivative and a preparation method and use thereof, so as to solve the technical defects existing in the prior art.

In a first aspect, the present invention provides a polysubstituted nitrogen-containing heterocyclic derivative having a structural formula of

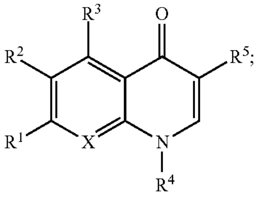

;

wherein $R^1$ is selected from one of the following groups: H, $CH_3$, $CH_3CH_2$, $CH_3O$, OH, F, Cl, Br, CN, $CF_3$, $CF_3O$, $NO_2$, 1-methyl-piperazin-4-yl, morpholine-4-yl, and piperazin-1-yl;

$R^2$ is selected from one of the following groups: H, $CH_3$, $CH_3CH_2$, $CH_3O$, OH, F, Cl, Br, CN, $CF_3$, $CF_3O$, and $NO_2$;

$R^3$ is selected from one of the following groups: H, $CH_3$, $CH_3CH_2$, $CH_3O$, OH, F, Cl, Br, CN, $CF_3$, $CF_3O$, and $NO_2$;

$R^4$ is selected from one of the following groups: H, $CH_3$, $CH_2CH_3$, $CH_2CH_2CH_3$, $CH(CH_3)_2$, tBu, $CH(CH_2)_2$, $CH_2C{=}CH$, $CH_2CH{=}CH_2$, $CH_3O$, $CH_2CH_2SO_2CH_3$, $CH_2CH_2SCH_3$, $CH_2CN$, $CH_2CF_3$, $CH_2CONH_2$, $C(CH_2)_2CN$, $CH_2Ph$, $CH_2CH_2Ph$, $CH_2$-4-MeO-Ph, $CH_2CH_2$-4-MeO-Ph, $CH_2$-3-MeO-Ph, $CH_2CH_2$-3-MeO-Ph, $CH_2$-4-F-Ph, $CH_2CH_2$-4-F-Ph, $CH_2$-4-$CF_3$-Ph, $CH_2CH_2$-4-$CF_3$-Ph, $CH(CH_3)Ph$, $CH_2$-4-OH-3-MeO-Ph, Ph, 4-MeO-Ph, 4-$CF_3$-Ph, 3-MeO-Ph, 3-$CF_3$-Ph, 2-MeO-Ph, 2-$CF_3$-Ph, 4-Me-Ph, 2-Me-Ph, 3-Me-Ph, 4-Cl-Ph, 3-Cl-Ph, 2-Cl-Ph, 4-F-Ph, 3-F-Ph, 2-F-Ph, 4-Br-Ph, 2-F-4-Cl-Ph, and 2,4-$Cl_2$-Ph;

$R^5$ is selected from one of the following groups: $CO_2Et$, $CO_2Me$, COOH, $CONHCH_2CH_3$, $CONHCH(CH_2)_2$, $CONHC(CH_2)_2CN$, $CONHCH_2CH_2SO_2CH_3$, $CONHCH_2CH_2SCH_3$, CONHNHCOPh, CONHNHCO-4-Py, $CONHCH_2Ph$, $CONHCH_2CH_2Ph$, $CONHCH_2$-4-MeO-Ph, $CONHCH_2CH_2$-4-MeO-Ph, $CONHCH_2$-4-OH-3-MeO-Ph, $CONHCH_2CH_2$-4-F-Ph, SPh, $SO_2Ph$, $SO_2$-4-Me-Ph, $SO_2$-4-Cl-Ph, $SO_2$-2-Me-Ph, $SO_2$-2-Cl-Ph, $SO_2$-3-Me-Ph, $SO_2$-3-Cl-Ph,

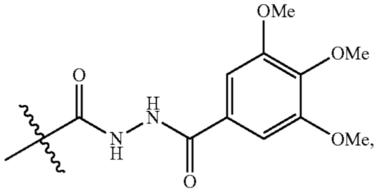

,

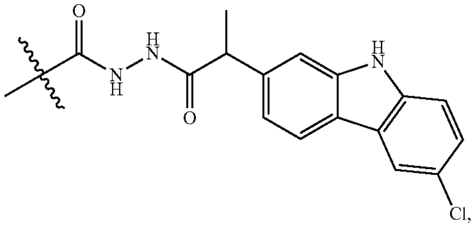

,

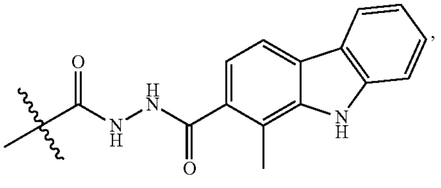

, and

-continued

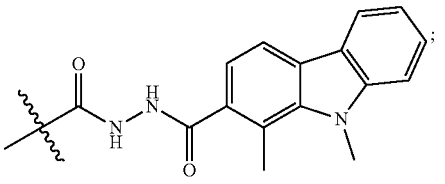

and

X is one of CH or N.

In a second aspect, the present invention also provides a method for preparing the polysubstituted nitrogen-containing heterocyclic derivative comprising the following steps:

taking a substituted aryl methyl ketone as a raw material to react with diethyl carbonate or dimethyl carbonate under a basic condition to obtain a substituted aryl acyl acetate;

condensing the substituted aryl acyl acetate with N,N-dimethylformamide dimethyl acetal to obtain a first intermediate;

reacting the first intermediate with a substituted amine under a basic condition to obtain a first polysubstituted nitrogen-containing heterocyclic derivative;

hydrolyzing the first polysubstituted nitrogen-containing heterocyclic derivative under an acidic or basic condition to obtain a second polysubstituted nitrogen-containing heterocyclic derivative;

subjecting the second polysubstituted nitrogen-containing heterocyclic derivative to a condensation reaction with a substituted amine under the action of a condensation agent to obtain a third polysubstituted nitrogen-containing heterocyclic derivative;

or, taking a substituted aryl methyl ketone as a raw material to obtain a bromo intermediate via a brominating reaction;

subjecting the bromo intermediate to a substitution reaction with a sodium substituted benzenesulfite or a sodium substituted thiophenolate to obtain a second intermediate or a third intermediate;

condensing the second intermediate or the third intermediate with N,N-dimethylformamide dimethyl acetal to obtain a fourth intermediate or a fifth intermediate;

subjecting the fourth intermediate or the fifth intermediate to a substitution cyclization reaction with a substituted amine under the action of a base to obtain a fourth polysubstituted nitrogen-containing heterocyclic derivative or a fifth polysubstituted nitrogen-containing heterocyclic derivative;

wherein the substituted aryl methyl ketone has the formula of

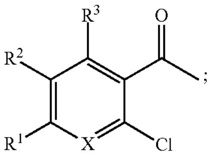

the substituted aryl acyl acetate has a structural formula of

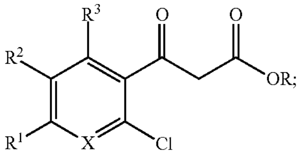

the first intermediate has a structural formula of

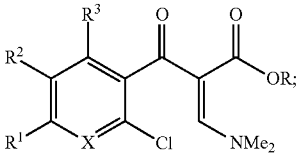

the first polysubstituted nitrogen-containing heterocyclic derivative has a structural formula of

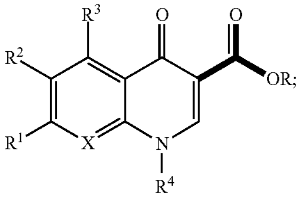

the second polysubstituted nitrogen-containing heterocyclic derivative has a structural formula of

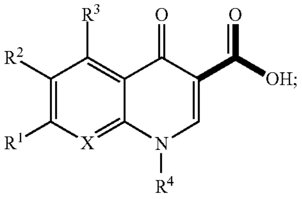

the third polysubstituted nitrogen-containing heterocyclic derivative has a structural formula of

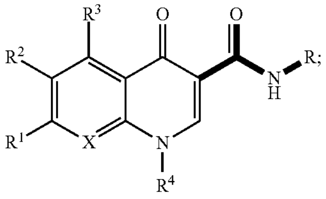

the bromo intermediate has a structural formula of

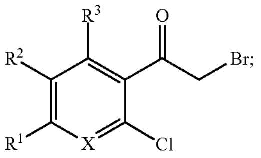

the second intermediate has a structural formula of

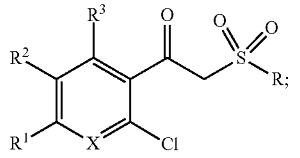

the third intermediate has a structural formula of

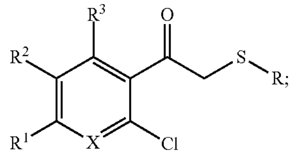

the fourth intermediate has a structural formula of

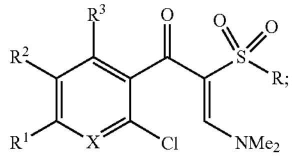

the fifth intermediate has a structural formula of

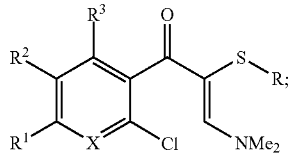

the fourth polysubstituted nitrogen-containing heterocyclic derivative has a structural formula of

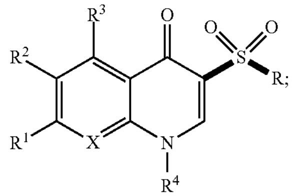

the fifth polysubstituted nitrogen-containing heterocyclic derivative has a structural formula of

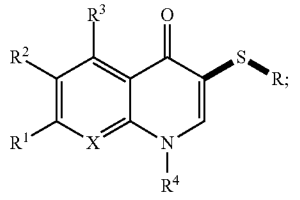

and wherein the R group is one of Me and Et.

In a third aspect, the present invention also provides a bactericide including the polysubstituted nitrogen-containing heterocyclic derivative.

In a fourth aspect, the present invention also provides use of the polysubstituted nitrogen-containing heterocyclic derivative or the bactericide for preventing and controlling plant bacterial diseases.

The polysubstituted nitrogen-containing heterocyclic derivative according to the present invention has the following beneficial effects compared to prior art:

the polysubstituted nitrogen-containing heterocyclic derivatives of the present invention have obvious bactericidal activity, and some compounds have significant bactericidal activity against diseases such as *E. carotovora, E. coli,* and *R. solanacearum,* which can be widely applied in the comprehensive prevention and control of agricultural and forestry bacterial diseases. The bactericides obtained by mixing the polysubstituted nitrogen-containing heterocyclic derivatives of the present invention with various adjuvants also have good bactericidal effects on *E. coli, E. carotovora, R. solanacearum,* etc.

BRIEF DESCRIPTION OF DRAWINGS

In order to provide a clearer explanation of the embodiments of the present invention or the technical solutions in the prior art, a brief introduction will be given below to the accompanying drawings required in the description of the embodiments or prior art. It is obvious that the drawings in the description below are only some embodiments of the present invention, and it would be obvious for a person skilled in the art to obtain other drawings according to these drawings without involving any inventive effort.

DETAILED DESCRIPTION OF THE EMBODIMENTS

Figure 1:
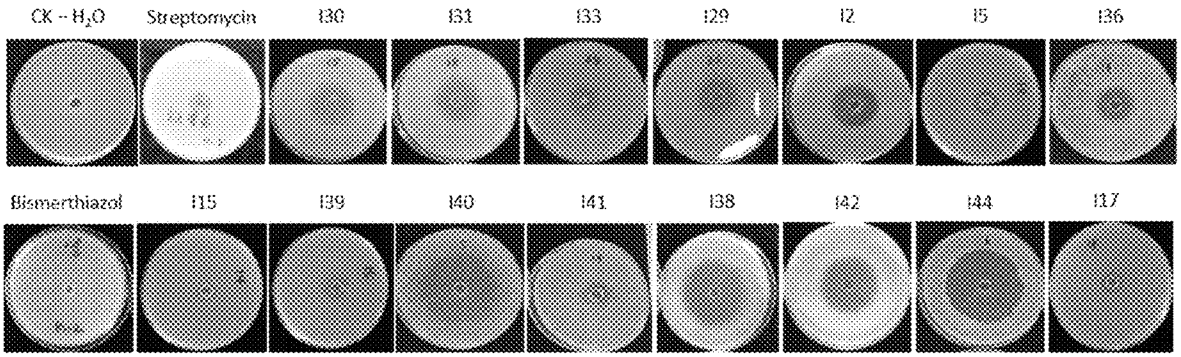
FIG. 1 shows the preliminary screening results of the bactericidal activity of different compounds against *R. solanacearum* in Example 1 of the present invention.

The technical solutions in the embodiments of the present invention will be described clearly and completely in conjunction with the embodiments of the present invention. Obviously, the described embodiments are only a part of the embodiments of the present invention, rather than all the embodiments. Based on the embodiments of the present invention, all Other embodiments obtained by a person of ordinary skill in the art without inventive effort fall within the scope of the present invention.

The present application provides a polysubstituted nitrogen-containing heterocyclic derivative that has a structural formula of

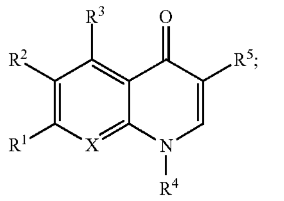

wherein $R^1$ is selected from one of the following groups: H, $CH_3$, $CH_3CH_2$, $CH_3O$, OH, F, Cl, Br, CN, $CF_3$, $CF_3O$, $NO_2$, 1-methyl-piperazin-4-yl, morpholine-4-yl, piperazin-1-yl; $R^2$ is selected from one of the following groups: H, $CH_3$, $CH_3CH_2$, $CH_3O$, OH, F, Cl, Br, CN, $CF_3$, $CF_3O$, and $NO_2$;

$R^3$ is selected from one of the following groups: H, $CH_3$, $CH_3CH_2$, $CH_3O$, OH, F, Cl, Br, CN, $CF_3$, $CF_3O$, and $NO_2$;

$R^4$ is selected from one of the following groups: H, $CH_3$, $CH_2CH_3$, $CH_2CH_2CH_3$, $CH(CH_3)_2$, tBu, $CH(CH_2)_2$, $CH_2C{\equiv}CH$, $CH_2CH{=}CH_2$, $CH_3O$, $CH_2CH_2SO_2CH_3$, $CH_2CH_2SCH_3$, $CH_2CN$, $CH_2CF_3$, $CH_2CONH_2$, $C(CH_2)_2CN$, $CH_2Ph$, $CH_2CH_2Ph$, $CH_2$-4-MeO-Ph, $CH_2CH_2$-4-MeO-Ph, $CH_2$-3-MeO-Ph, $CH_2CH_2$-3-MeO-Ph, $CH_2$-4-F-Ph, $CH_2CH_2$-4-F-Ph, $CH_2$-4-$CF_3$-Ph, $CH_2CH_2$-4-$CF_3$-Ph, $CH(CH_3)Ph$, $CH_2$-4-OH-3-MeO-Ph, Ph, 4-MeO-Ph, 4-$CF_3$-Ph, 3-MeO-Ph, 3-$CF_3$-Ph, 2-MeO-Ph, 2-$CF_3$-Ph, 4-Me-Ph, 2-Me-Ph, 3-Me-Ph, 4-Cl-Ph, 3-Cl-Ph, 2-Cl-Ph, 4-F-Ph, 3-F-Ph, 2-F-Ph, 4-Br-Ph, 2-F-4-Cl-Ph, and 2,4-$Cl_2$-Ph;

$R^5$ is selected from one of the following groups: $CO_2Et$, $CO_2Me$, COOH, $CONHCH_2CH_3$, $CONHCH(CH_2)_2$, $CONHC(CH_2)_2CN$, $CONHCH_2CH_2SO_2CH_3$, $CONHCH_2CH_2SCH_3$, CONHNHCOPh, CONHNHCO-4-Py, $CONHCH_2Ph$, $CONHCH_2CH_2Ph$, $CONHCH_2$-4-MeO-Ph, $CONHCH_2CH_2$-4-MeO-Ph, $CONHCH_2$-4-OH-3-MeO-Ph, $CONHCH_2CH_2$-4-F-Ph, SPh, $SO_2Ph$, $SO_2$-4-Me-Ph, $SO_2$-4-Cl-Ph, $SO_2$-2-Me-Ph, $SO_2$-2-Cl-Ph, $SO_2$-3-Me-Ph, $SO_2$-3-Cl-Ph,

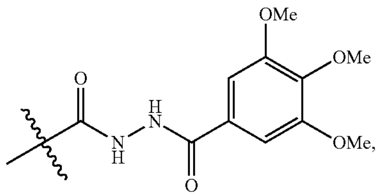

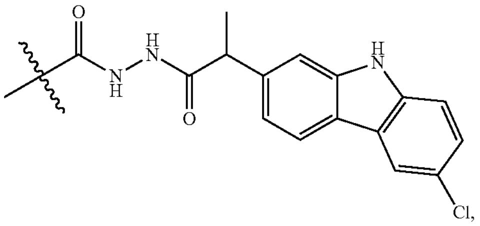

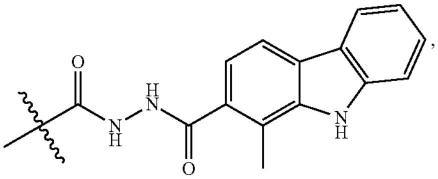

, and

-continued

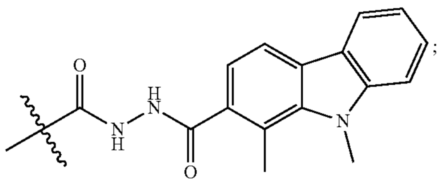

;

and

X is one of CH or N.

In the above examples, tBu represents tert-butyl; Ph represents phenyl; Me represents methyl; Et represents ethyl; Py represents pyridyl.

Heterocyclic nitrogen-containing compounds are common molecular scaffolds widely existing in natural products and synthetic drugs, usually have important physiological and biochemical functions, and have very important applications in medicinal chemistry, agricultural and food chemistry, biochemistry, and polymer materials. In the present application, the novel structures of the natural nitrogen-containing heterocyclic molecules are designed to obtain the polysubstituted nitrogen-containing heterocyclic derivatives. The polysubstituted nitrogen-containing heterocyclic derivatives have obvious bactericidal activity, and some compounds have significant bactericidal activity against diseases such as *E. carotovora, E. coli,* and *R. solanacearum,* which can be widely applied in the comprehensive prevention and control of agricultural and forestry bacterial diseases.

The polysubstituted nitrogen-containing heterocyclic derivatives of the present invention also include stereoisomers, tautomers, solvates, or pesticidally acceptable salts of the compounds of the formula.

In some embodiments, the polysubstituted nitrogen-containing heterocyclic derivative is selected from any one of the following compounds:

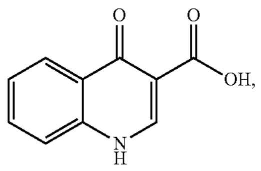

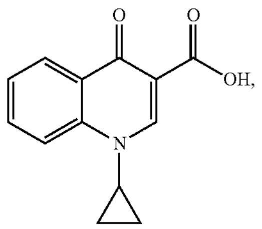

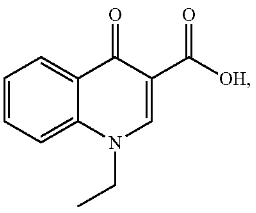

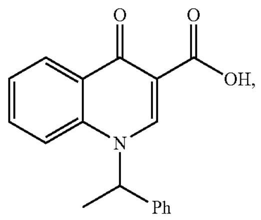

-continued
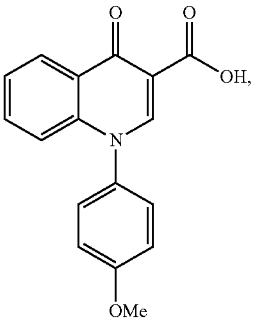
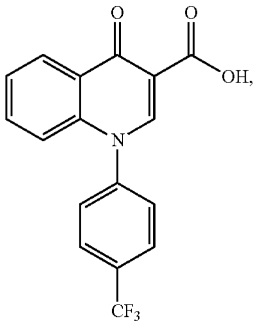
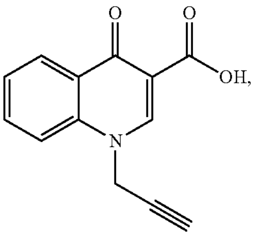
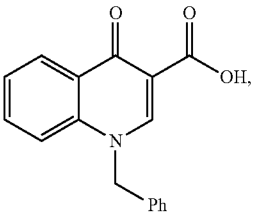
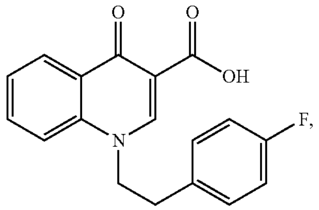
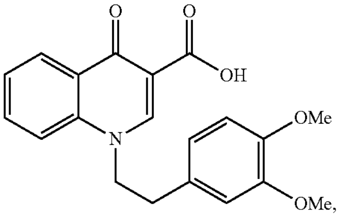
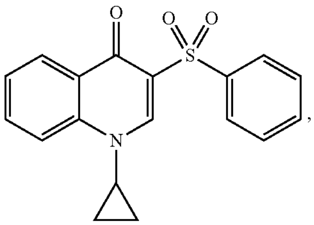
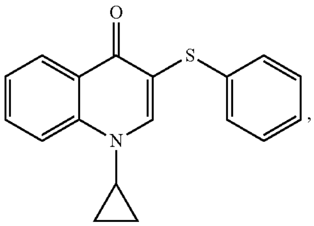
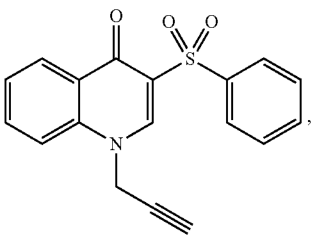
-continued
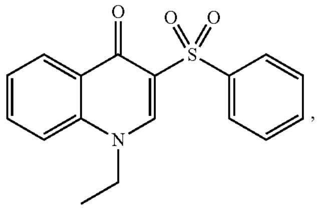
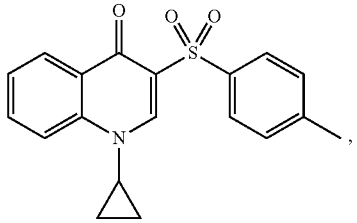
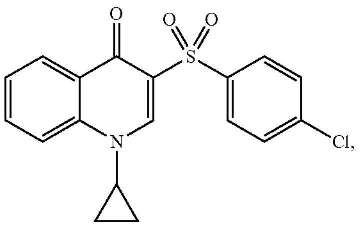
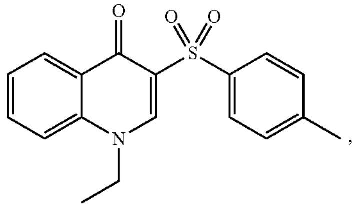
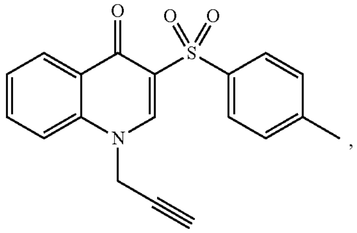
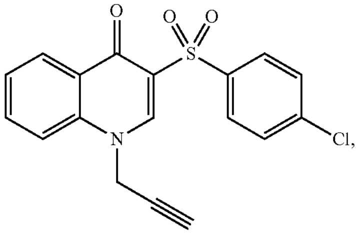
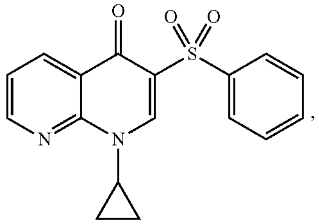

-continued
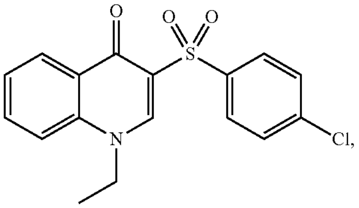
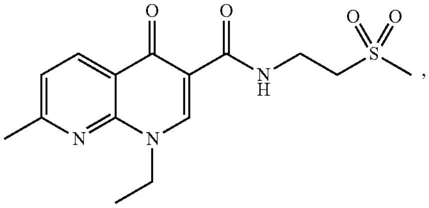
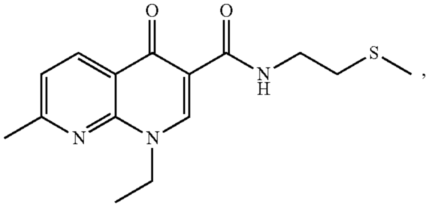
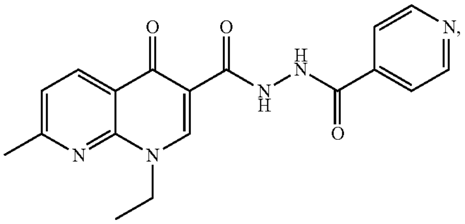
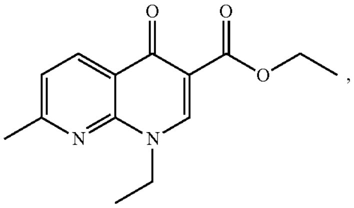
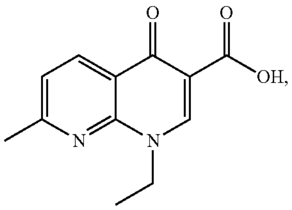
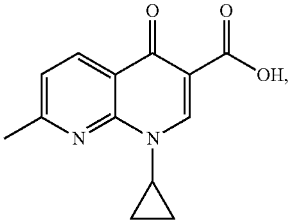
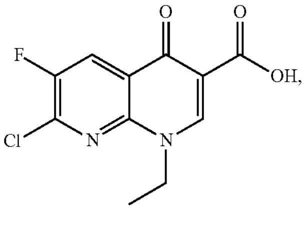
-continued
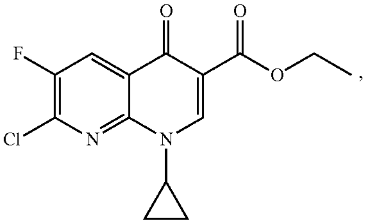
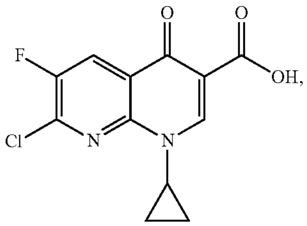
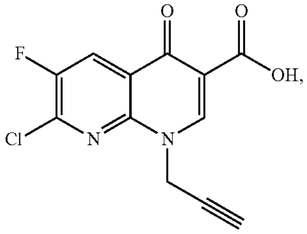
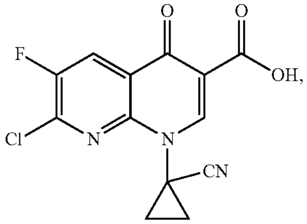
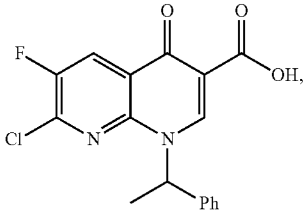
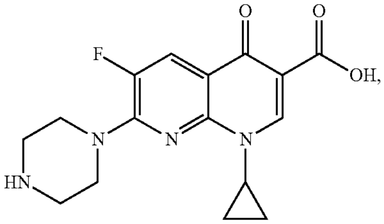
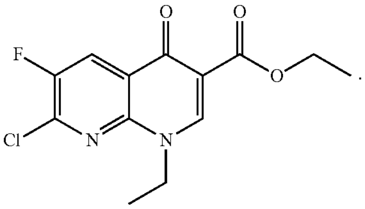
Based on the same inventive concept, the embodiments of the present application also provide a method for preparing the above-mentioned polysubstituted nitrogen-containing heterocyclic derivative, comprising the following steps:

taking a substituted aryl methyl ketone as a raw material to react with diethyl carbonate or dimethyl carbonate under a basic condition to obtain a substituted aryl acyl acetate;

condensing the substituted aryl acyl acetate with N,N-dimethylformamide dimethyl acetal to obtain a first intermediate;

reacting the first intermediate with a substituted amine under a basic condition to obtain a first polysubstituted nitrogen-containing heterocyclic derivative;

hydrolyzing the first polysubstituted nitrogen-containing heterocyclic derivative under an acidic or basic condition to obtain a second polysubstituted nitrogen-containing heterocyclic derivative;

subjecting the second polysubstituted nitrogen-containing heterocyclic derivative to a condensation reaction with a substituted amine under the action of a condensation agent to obtain a third polysubstituted nitrogen-containing heterocyclic derivative;

or, taking a substituted aryl methyl ketone as a raw material to obtain a bromo intermediate via a brominating reaction;

subjecting the bromo intermediate to a substitution reaction with a sodium substituted benzenesulfite or a sodium substituted thiophenolate to obtain a second intermediate or a third intermediate;

condensing the second intermediate or the third intermediate with N,N-dimethylformamide dimethyl acetal to obtain a fourth intermediate or a fifth intermediate;

subjecting the fourth intermediate or the fifth intermediate to a substitution cyclization reaction with a substituted amine under the action of a base to obtain a fourth polysubstituted nitrogen-containing heterocyclic derivative or a fifth polysubstituted nitrogen-containing heterocyclic derivative;

wherein the substituted aryl methyl ketone has the formula of

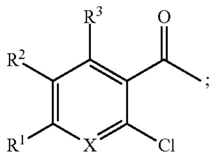

the substituted aryl acyl acetate has a structural formula of

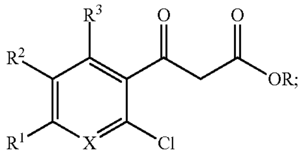

the first intermediate has a structural formula of

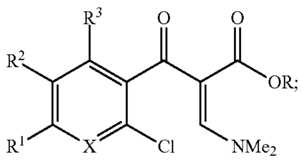

the first polysubstituted nitrogen-containing heterocyclic derivative has a structural formula of

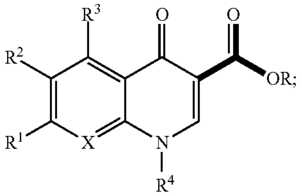

the second polysubstituted nitrogen-containing heterocyclic derivative has a structural formula of

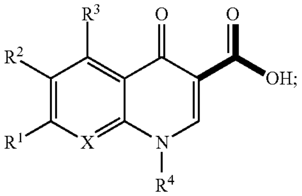

the third polysubstituted nitrogen-containing heterocyclic derivative has a structural formula of

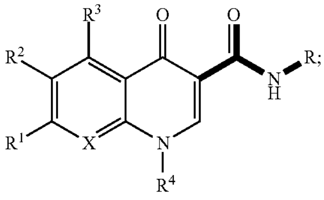

the bromo intermediate has a structural formula of

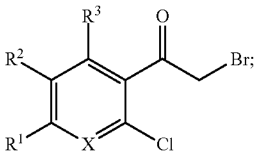

the second intermediate has a structural formula of

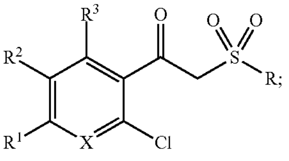

the third intermediate has a structural formula of

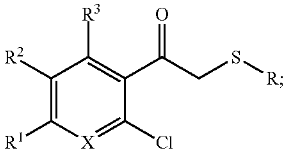

the fourth intermediate has a structural formula of

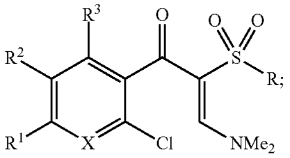

the fifth intermediate has a structural formula of

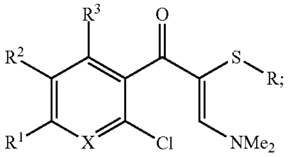

the fourth polysubstituted nitrogen-containing heterocyclic derivative has a structural formula of

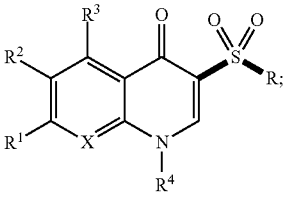

the fifth polysubstituted nitrogen-containing heterocyclic derivative has a structural formula of

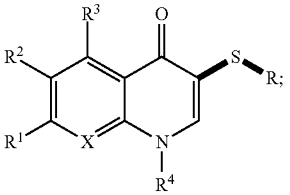

and wherein the R group is one of Me and Et.

Specifically, the reaction formula occurring during the preparation of the above-mentioned polysubstituted nitrogen-containing heterocyclic derivative is:

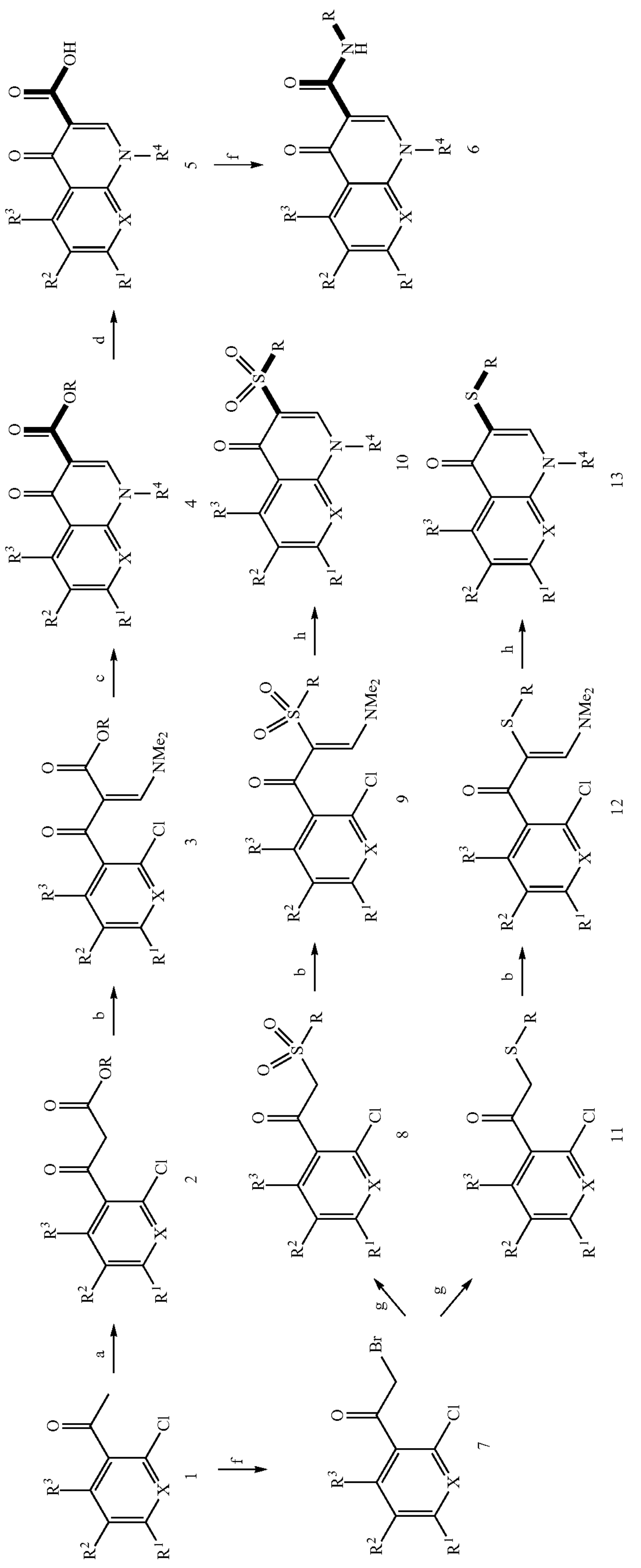
a
b
c
d
f
f
g
g
b
b
h
h
1
2
3
4
5
6
7
8
9
10
11
12
13

Specifically, a substituted aryl methyl ketone 1 is reacted to obtain a substituted aryl acyl acetate 2; the substituted aryl acyl acetate 2 is condensed with N,N-dimethylformamide dimethyl acetal to obtain a first intermediate 3; the first intermediate 3 is reacted with a substituted amine under a basic condition to obtain a first polysubstituted nitrogen-containing heterocyclic derivative 4; the first polysubstituted nitrogen-containing heterocyclic derivative 4 is hydrolyzed under an acidic or basic condition to obtain a second polysubstituted nitrogen-containing heterocyclic derivative 5; the second polysubstituted nitrogen-containing heterocyclic derivative 5 is subjected to a condensation reaction with a substituted amine under the action of a condensation agent to obtain a third polysubstituted nitrogen-containing heterocyclic derivative 6.

Or, the substituted aryl methyl ketone 1 is subjected to a brominating reaction to give a bromo intermediate 7; the bromo intermediate 7 is subjected to a substitution reaction with sodium substituted benzenesulfite or sodium substituted thiophenolate to obtain a second intermediate 8 or a third intermediate 11; the second intermediate 8 or the third intermediate 11 is condensed with N,N-dimethylformamide dimethyl acetal to obtain a fourth intermediate 9 or a fifth intermediate 12; the fourth intermediate 9 or the fifth intermediate 12 is subjected to a substitution cyclization reaction with a substituted amine under the action of a base to obtain the fourth polysubstituted nitrogen-containing heterocyclic derivative 10 or the fifth polysubstituted nitrogen-containing heterocyclic derivative 13.

In some embodiments, in the step of taking a substituted aryl methyl ketone as a raw material to react with diethyl carbonate or dimethyl carbonate under a basic condition to obtain a substituted aryl acyl acetate, the reaction temperature is 0-50° C.; the reaction solvent is one of acetonitrile, 1,2-dichloroethane and tetrahydrofuran; the base is one of sodium hydroxide, potassium hydroxide or sodium hydride.

In some embodiments, in the step of condensing the substituted aryl acyl acetate with N,N-dimethylformamide dimethyl acetal to obtain a first intermediate, the reaction temperature is 20-100° C.; the reaction solvent is one of acetonitrile, 1,2-dichloroethane, toluene, xylene, and chlorobenzene; and the catalyst is acetic acid.

In some embodiments, in the step of reacting the first intermediate with a substituted amine under a basic condition to obtain a first polysubstituted nitrogen-containing heterocyclic derivative, the reaction temperature is 25-60° C.; the reaction solvent is one of acetonitrile, 1,2-dichloroethane, toluene, xylene, chlorobenzene, and dioxane; and the base is one of sodium hydroxide, potassium hydroxide, or sodium hydride.

In some embodiments, in the step of hydrolyzing the first polysubstituted nitrogen-containing heterocyclic derivative under an acidic or basic condition to obtain a second polysubstituted nitrogen-containing heterocyclic derivative, the reaction solvent is one of methanol, ethanol, isopropanol, and tetrahydrofuran; the base is one of sodium hydroxide, potassium hydroxide, and potassium carbonate; the acid is hydrochloric acid.

In some embodiments, in the step of subjecting the second polysubstituted nitrogen-containing heterocyclic derivative to a condensation reaction with a substituted amine under the action of a condensation agent to obtain a third polysubstituted nitrogen-containing heterocyclic derivative, the reaction temperature is 20-50° C.; the reaction solvent is any one of acetonitrile, 1,2-dichloroethane, N,N-dimethylformamide, N,N-dimethylacetamide, tetrahydrofuran, dichloromethane and ethyl acetate; the condensation agent is one of TBTU (O-benzotriazole-N,N,N',N'-tetramethylurea tetrafluoroborate), HOBt/EDCI (1-hydroxybenzotriazole/1-(3-dimethylaminopropyl)-3-ethylcarbodiimide, both used as condensation agents), HATU (2-(7-azabenzotriazole)-N,N,N',N'-tetramethylurea hexafluorophosphate), HDTU, DCC/DMAP (dicyclohexylcarbodiimide/4-dimethylaminopyridine, both used as condensation agents), DIC/DMAP (diisopropylcarbodiimide/4-dimethylaminopyridine, both used as condensation agents), and EDCI (1-(3-dimethylaminopropyl)-3-ethylcarbodiimide).

In some embodiments, in the step of taking a substituted aryl methyl ketone as a raw material to obtain a bromo intermediate via a brominating reaction, the reaction temperature is 10-60° C.; the reaction solvent is one of acetonitrile, tetrahydrofuran, carbon tetrachloride, 1,2-dichloroethane, and dichloromethane; the brominating reagent is one of N-bromosuccinimide, copper bromide, sodium bromide, bromine, and dibromohydantoin.

In some embodiments, in the step of subjecting the bromo intermediate to a substitution reaction with a sodium substituted benzenesulfite or a sodium substituted thiophenolate to obtain a second intermediate or a third intermediate, the reaction temperature is 40-90° C.; the reaction solvent is one of acetonitrile, ethanol, methanol, acetone, ethyl acetate, 1,2-dichloroethane, tetrahydrofuran, N,N-dimethylformamide, and N,N-dimethylacetamide.

In some embodiments, in the step of condensing the second intermediate or the third intermediate with N,N-dimethylformamide dimethyl acetal to obtain a fourth intermediate or a fifth intermediate, the reaction temperature is 20-100° C.; the reaction solvent is one of acetonitrile, 1,2-dichloroethane, toluene, xylene, and chlorobenzene; the catalyst is acetic acid.

In some embodiments, in the step of subjecting the fourth intermediate or the fifth intermediate to a substitution cyclization reaction with a substituted amine to obtain a fourth polysubstituted nitrogen-containing heterocyclic derivative or a fifth polysubstituted nitrogen-containing heterocyclic derivative, the reaction temperature is 50-150° C.; the reaction solvent is one of dioxane, toluene, xylene, chlorobenzene, dimethyl sulfoxide, N,N-dimethylformamide, and N,N-dimethylacetamide; the base is one of potassium carbonate, cesium carbonate, and sodium carbonate.

Based on the same inventive concept, the embodiments of the present application also provide a bactericide comprising the above-mentioned polysubstituted nitrogen-containing heterocyclic derivatives.

In some embodiments, an adjuvant is further included, and the mass fraction of the polysubstituted nitrogen-containing heterocyclic derivative in the bactericide is 0.5-99.99%, preferably 5-45%.

In some embodiments, the adjuvant comprises one or more of isopropyl alcohol, glycerol, turpentine, propanol, 1, xylene, chlorobenzene, 1,2-dichloroethane, 1,2-dibromoethane, toluene, methanol, ethanol, N,N-dimethylformamide, ethyl acetate, acetone, butanone, cyclohexanone, dimethylsulfoxide, and paraffin;

or the adjuvant comprises one or more of kaolin, bentonite, clay, diatomite, montmorillonite, attapulgite, dolomite, quartz, calcium carbonate, oxide film, talc, and attapulgite;

or the adjuvant comprises one or more of alkyl sulfonate salt, alkyl sulfonate ester, alkyl aryl sulfonate salt, polyoxyethylene sorbitol ester, polyoxyethylene-fatty alcohol ether, polyoxyethylene-fatty acid ester, aralkyl polyethylene glycol ether, fluoroalkyl sulfonate, alkyl sulfate, lignosulfonate, polyethylene glycol, and rhamnolipid;

or, the adjuvant comprises one or more of polyvinyl alcohol, carboxymethyl cellulose, and gum arabic;

or, the adjuvant comprises one or more of an inorganic dye, an organic dye, and a trace nutrient.

In some embodiments, the bactericide is formulated as any one of water-dispersible granules, an aqueous emulsion, a suspension, a wettable powder, or a nano controlled release agent.

Based on the same inventive concept, the embodiments of the present application also provide use of the above-mentioned polysubstituted nitrogen-containing heterocyclic derivative or the above-mentioned bactericide for preventing and controlling plant bacterial diseases.

In some embodiments, the bacterial diseases comprise one or more of diseases caused by ginger bacterial wilt, tomato bacterial wilt, chili bacterial wilt, tobacco bacterial wilt, potato bacterial wilt, and peanut bacterial wilt, soft rot of fruits and vegetables, canker disease, and rice bacterial leaf blight.

The following further illustrates the polysubstituted nitrogen-containing heterocyclic derivative of the present application, preparation method, bactericide, and use thereof by means of specific embodiments. This section further explains the content of the present invention in conjunction with specific embodiments, but should not be understood as a limitation of the present invention. Unless otherwise specified, the technical means used in the examples are conventional means well known to a person skilled in the art. Unless otherwise indicated, the reagents, methods, and equipment used herein are those conventional in the art.

EXAMPLE 1

This example of the present application provides a polysubstituted nitrogen-containing heterocyclic derivative that has a structural formula of:

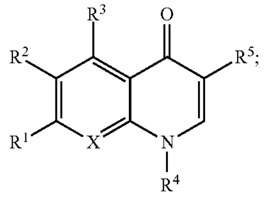

wherein $R^1$, $R^2$, $R^3$, $R^4$, $R^5$ groups are as shown in Table 1 below.

TABLE 1

Substituents of different polysubstituted nitrogen-containing heterocyclic derivatives

| Compound No. | Substituent X | $R^1$ | $R^2$ | $R^3$ | $R^4$ | $R^5$ |
|---|---|---|---|---|---|---|
| I1 | CH | H | H | H | H | COOH |
| I2 | CH | H | H | H | Cyclopropyl | COOH |
| I3 | CH | H | H | H | Et | COOH |
| I4 | CH | H | H | H | Et | COOEt |
| I5 | CH | H | H | H | 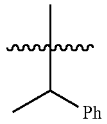 | COOH |
| I6 | CH | H | H | H | 4-MeOPh | COOH |
| I7 | CH | H | H | H | 4-$CF_3$Ph | COOH |
| I8 | CH | H | H | H | Propargyl | COOH |
| I9 | CH | H | H | H | $PhCH_2$ | COOH |
| I10 | CH | H | H | H | 4-F-$PhCH_2CH_2$ | COOH |
| I11 | CH | H | H | H | 3,4-$(MeO)_2$-$PhCH_2CH_2$ | COOH |
| I12 | CH | $CH_3$ | H | H | H | COOH |
| I13 | CH | $CH_3$ | H | H | Cyclopropyl | COOH |
| I14 | CH | H | H | H | Cyclopropyl | $PhSO_2$ |
| I15 | CH | H | H | H | Cyclopropyl | PhS |
| I16 | CH | H | H | H | Propargyl | $PhSO_2$ |
| I17 | CH | H | H | H | Et | $PhSO_2$ |
| I18 | CH | H | H | H | Cyclopropyl | 4-$MePhSO_2$ |
| I19 | CH | H | H | H | Cyclopropyl | 4-$ClPhSO_2$ |
| I20 | CH | H | H | H | Et | 4-$MePhSO_2$ |
| I21 | CH | H | H | H | Propargyl | 4-$MePhSO_2$ |
| I22 | CH | H | H | H | Propargyl | 4-$ClPhSO_2$ |
| I23 | N | H | H | H | Cyclopropyl | $PhSO_2$ |
| I24 | N | H | H | H | Cyclopropyl | PhS |
| I25 | CH | H | H | H | Et | 4-$ClPhSO_2$ |
| I26 | CH | H | H | H | Et | PhS |
| I27 | N | $CH_3$ | H | H | Et | $CONH(CH_2)_2SO_2Me$ |
| I28 | N | $CH_3$ | H | H | Et | $CONH(CH_2)_2SMe$ |

TABLE 1-continued

Substituents of different polysubstituted nitrogen-containing heterocyclic derivatives

| Compound No. | X | $R^1$ | $R^2$ | $R^3$ | $R^4$ | $R^5$ |
|---|---|---|---|---|---|---|
| I29 | N | $CH_3$ | H | H | Et | 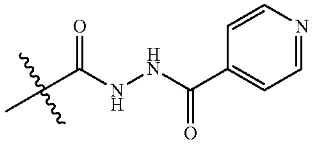 [SMILES: *C(=O)NNC(=O)c1ccncc1] |
| I30 | N | $CH_3$ | H | H | Et | 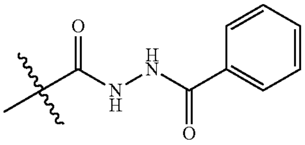 [SMILES: *C(=O)NNC(=O)c1ccccc1] |
| I31 | N | $CH_3$ | H | H | Et | 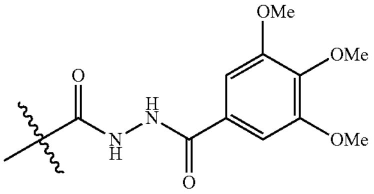 [SMILES: *C(=O)NNC(=O)c1cc(OC)c(OC)c(OC)c1] |
| I32 | N | $CH_3$ | H | H | Et | 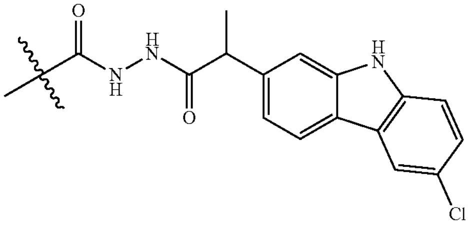 [SMILES: *C(=O)NNC(=O)C(C)c1ccc2c(c1)[nH]c1ccc(Cl)cc12] |
| I33 | N | $CH_3$ | H | H | Et | 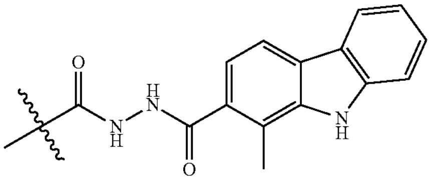 |
| I34 | N | $CH_3$ | H | H | Et | 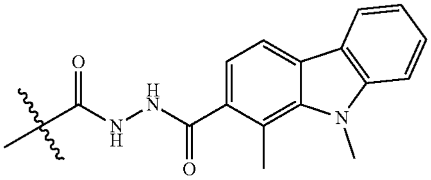 [SMILES: *C(=O)NNC(=O)c1ccc2c3ccccc3n(C)c2c1C] |
| I35 | N | $CH_3$ | H | H | Et | COOEt |
| I36 | N | $CH_3$ | H | H | Et | COOH |
| I37 | N | $CH_3$ | H | H | Cyclopropyl | COOH |
| I38 | N | Cl | F | H | Et | COOH |
| I39 | N | Cl | F | H | Cyclopropyl | COOEt |
| I40 | N | Cl | F | H | Cyclopropyl | COOH |
| I41 | N | Cl | F | H | Propargyl | COOH |
| I42 | N | Cl | F | H | 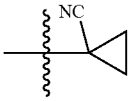 [SMILES: *C1(C#N)CC1] | COOH |

TABLE 1-continued

| Substituents of different polysubstituted nitrogen-containing heterocyclic derivatives | | | | | | |
|---|---|---|---|---|---|---|
| Compound | Substituent | | | | | |
| No. | X | $R^1$ | $R^2$ | $R^3$ | $R^4$ | $R^5$ |
| I43 | N | Cl | F | H | 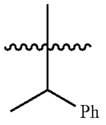 [SMILES: *C(C)c1ccccc1] | COOH |
| I44 | N | Piperazin-1-yl | F | H | Cyclopropyl | COOH |
| I45 | N | Cl | F | H | Et | COOEt |

EXAMPLE 2

This example of the present application provides a polysubstituted nitrogen-containing heterocyclic derivative, the specific structure of which is shown in compound I2 of Table 1, and the preparation reaction formula thereof is:

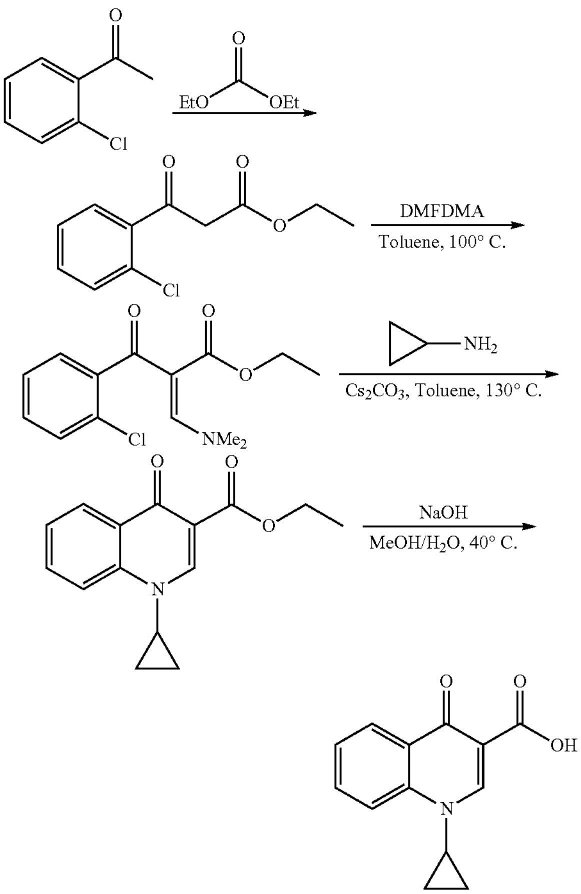

A specific method for the preparation of compound I2 included: (1) compound o-chloroacetophenone (10 mmol, 1 eq) was added into a round bottom flask containing 15 mL of THF (tetrahydrofuran), and stirred to be dissolved; then NaH (12 mmol, 1.2 eq) was added into the reaction bottle under continuous stirring, and stirred at normal temperature for 30 minutes; diethyl carbonate (12 mmol, 1.2 eq) was then added, heated to reflux; the reaction was monitored by TLC until the reaction was complete; the reaction was quenched with saturated ammonium chloride; the reaction product was extracted with EA, washed with water, dried and concentrated to give an intermediate ethyl o-chlorobenzoylacetate. (2) The above-mentioned ethyl o-chlorobenzoylacetate (6 mmol) was taken to be dissolved in 15 mL of toluene, and DMFDMA (N,N-dimethylformamide dimethyl acetal, 7.2 mmol) was added; then the temperature of the mixture was slowly increased to 100° C. for reaction; the reaction was monitored by TLC until the reaction was complete; the reaction product was concentrated under reduced pressure to obtain a crude product for later use. (3) 15 mL of toluene, cyclopropylamine (6 mmol) and cesium carbonate (6 mmol) were successively added to the above-mentioned crude product; the temperature was increased to 130° C.; the mixture was stirred for reaction until the conversion of the substrate was complete; after cooling, the reaction solution was poured into 25 mL of ice water; the reaction product was extracted with ethyl acetate, washed with water, dried, and concentrated to obtain an intermediate ethyl N-(cyclopropyl)-4-oxo-1,4-dihydroquinoline-3-carboxylate; (4) the intermediate ethyl N-(cyclopropyl)-4-oxo-1,4-dihydroquinoline-3-carboxylate obtained in step (3) was hydrolyzed under a basic (sodium hydroxide) condition; the pH was adjusted to 2-3 with dilute hydrochloric acid under an ice bath condition to precipitate a solid, and the target product was given through suction filtration. Analytical data for target compound I2: MS (ESI) m/z 230.3 $(M+H)^+$, calcd. for $C_{13}H_{11}NO_3$ m/z=229.1.

EXAMPLE 3

This example of the present application provides a polysubstituted nitrogen-containing heterocyclic derivative, the specific structure of which is shown in compound I5 of Table 1, and the preparation reaction formula thereof is:

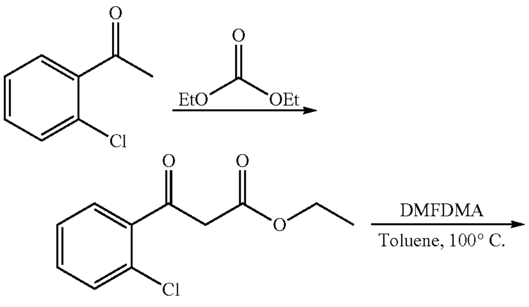

-continued

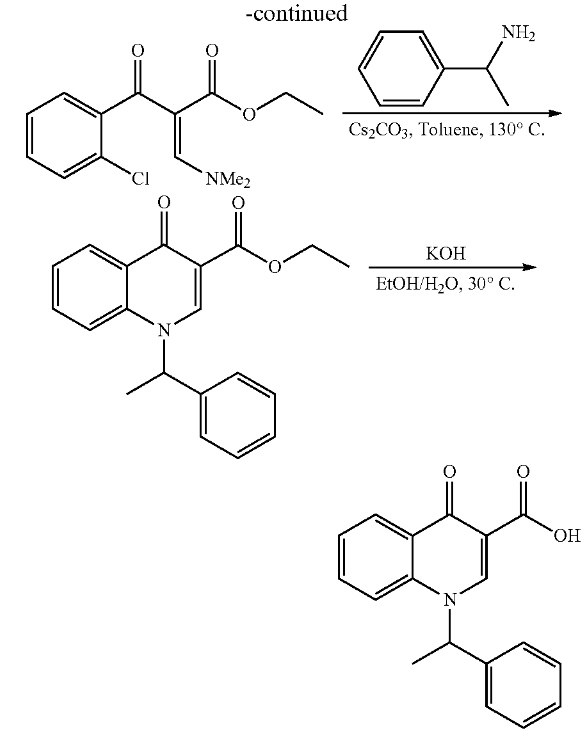

A specific method for the preparation of compound I5 included: steps (1), (2) and (3) were referred to the method of example 2, and cyclopropylamine was replaced with α-phenethylamine in step (3) to prepare an intermediate ethyl N-(1-phenylethyl)-4-oxo-1,4-dihydroquinoline-3-carboxylate. (4) The obtained intermediate ethyl N-(1-phenylethyl)-4-oxo-1,4-dihydroquinoline-3-carboxylate was hydrolyzed under the conditions of potassium hydroxide and ethanol; after the reaction was completed, the pH was adjusted to 2-3 with dilute hydrochloric acid under an ice bath condition; the reaction product was extracted with dichloromethane, washed with water, dried, and concentrated to obtain the target product. Analytical data for target compound I5: MS (ESI) m/z 316.4 $(M+Na)^+$, calcd. for $C_{18}H_{15}NO_3$ m/z=293.1.

EXAMPLE 4

This example of the present application provides a poly-substituted nitrogen-containing heterocyclic derivative, the specific structure of which is shown in compound I6 of Table 1, and the preparation reaction formula thereof is:

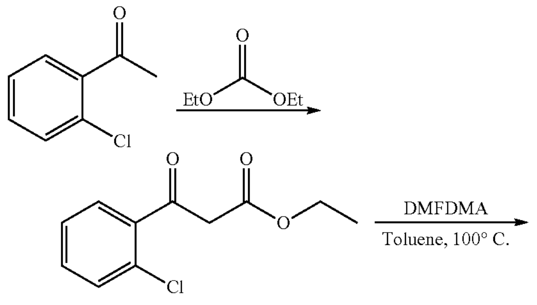

-continued

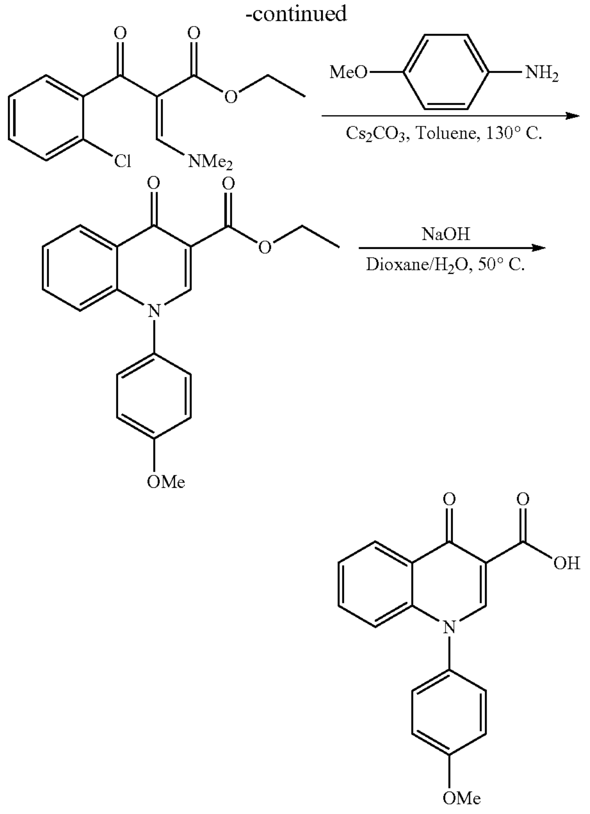

A specific method for the preparation of compound I6 included: steps (1) and (2) were referred to the method of example 2. (3) 15 mL of toluene, p-anisidine (6 mmol) and cesium carbonate (6 mmol) were successively added to the above-mentioned crude product; the temperature was increased to 130° C.; the mixture was stirred for reaction until the conversion of the substrate was complete; after cooling, the reaction solution was poured into 25 mL of ice water; the reaction product was extracted with ethyl acetate, washed with water, dried, and concentrated to obtain an intermediate ethyl N-(4-methoxyphenyl)-4-oxo-1,4-dihydroquinoline-3-carboxylate; (4) the intermediate ethyl N-(4-methoxyphenyl)-4-oxo-1,4-dihydroquinoline-3-carboxylate obtained in step (3) was hydrolyzed under a basic (sodium hydroxide) condition; the pH was adjusted to about 2-3 with dilute hydrochloric acid under an ice bath condition to precipitate a solid, and the target product was given through suction filtration. Analytical data for target compound I6: MS (ESI) m/z 296.4 $(M+H)^+$, calcd. for $C_{17}H_{13}NO_4$ m/z=295.1.

EXAMPLE 5

This example of the present application provides a poly-substituted nitrogen-containing heterocyclic derivative, the specific structure of which is shown in compound I10 of Table 1, and the preparation reaction formula thereof is:

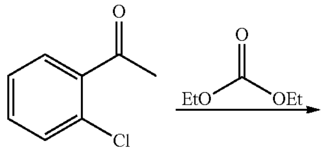

-continued

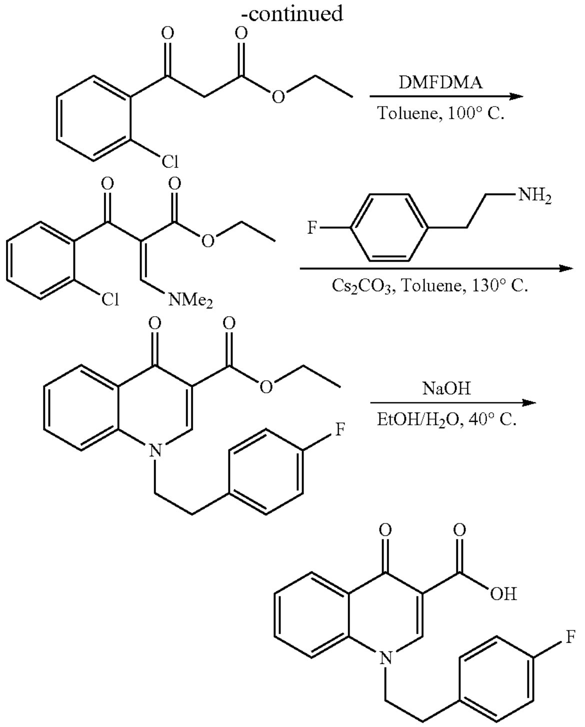

A specific method for the preparation of compound I10 included: steps (1) and (2) were referred to the method of example 2. (3) 15 mL of toluene, p-fluorophenethylamine (6 mmol), and cesium carbonate (6 mmol) were successively added to the above-mentioned crude product; the temperature was increased to 130° C.; the mixture was stirred for reaction until the conversion of the substrate was complete. After cooling, the reaction solution was poured into 25 mL of ice water; the reaction product was extracted with ethyl acetate, washed with water, dried, and concentrated to obtain an intermediate ethyl N-(4-fluorophenylethyl)-4-oxo-1,4-dihydroquinoline-3-carboxylate. (4) The intermediate ethyl N-(4-fluorophenylethyl)-4-oxo-1,4-dihydroquinoline-3-carboxylate obtained in step (3) was hydrolyzed under a sodium hydroxide condition; the pH was adjusted to about 2-3 with dilute hydrochloric acid under an ice bath condition; and the reactant was extracted with dichloromethane, washed with water, dried, and concentrated to obtain the target product. Analytical data for target compound I10: MS (ESI) m/z 312.2 $(M+H)^+$, calcd. for $C_{18}H_{14}FNO_3$ m/z=311.1.

EXAMPLE 6

This example of the present application provides a poly-substituted nitrogen-containing heterocyclic derivative, the specific structure of which is shown in compound I14 of Table 1, and the preparation reaction formula thereof is:

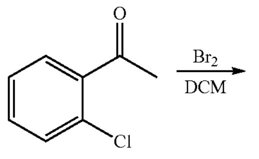

-continued

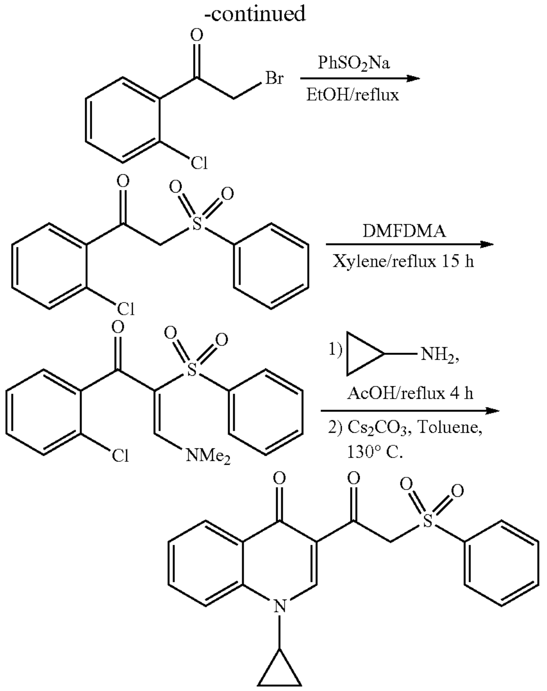

A specific method for the preparation of compound I14 included: (1) 10 mmol of o-chloroacetophenone was dissolved in 20 mL of dichloromethane; a solution of 20 mmol of liquid bromine in dichloromethane was added dropwise under an ice bath condition; after the addition, the mixture was stirred for reaction at room temperature; the reaction was monitored by TLC until the reaction was complete; the reaction product was washed with water, dried, and concentrated to obtain a bromoacetophenone intermediate. (2) 6 mmol of bromoacetophenone intermediate was dissolved in 20 mL of absolute ethanol; then 6.6 mmol of sodium benzenesulfinate was added, slowly heated to reflux; the reaction was monitored by TLC until the reaction was complete; the reaction product was concentrated and added with 20 mL of water; the mixture was extracted with dichloromethane, washed with water, dried, and concentrated to obtain an intermediate 1-(2-chlorophenyl)-2-(phenylsulfonyl)ethenone. (3) The above-mentioned 1-(2-chlorophenyl)-2-(phenylsulfonyl)ethanone (5 mmol) was taken and dissolved in 15 mL of xylene; DMFDMA (6 mmol) was added; then the mixture was slowly warmed up to reflux; the reaction was monitored by TLC until the reaction was complete; the reaction product was concentrated under reduced pressure to obtain a crude product for later use. (4) To the above crude product, 8-10 mL of acetic acid and 5.5 mmol of cyclopropylamine were added and heated to reflux for about 4 h; the reaction product was concentrated to dryness; then 20 mL of toluene, 6 mmol of cesium carbonate were added, and heated to reflux; the reaction was monitored by TLC until the reaction was complete; the reaction product was cooled, poured into ice water, extracted with dichloromethane, washed with water, dried, concentrated, and separated by column chromatography to obtain the target product. Analytical data for target compound I14 MS (ESI) m/z 326.3 $(M+H)^+$, calcd. for $C_{18}H_{15}NO_3$ m/z=325.1.

EXAMPLE 7

This example of the present application provides a poly-substituted nitrogen-containing heterocyclic derivative, the specific structure of which is shown in compound I24 of Table 1, and the preparation reaction formula thereof is:

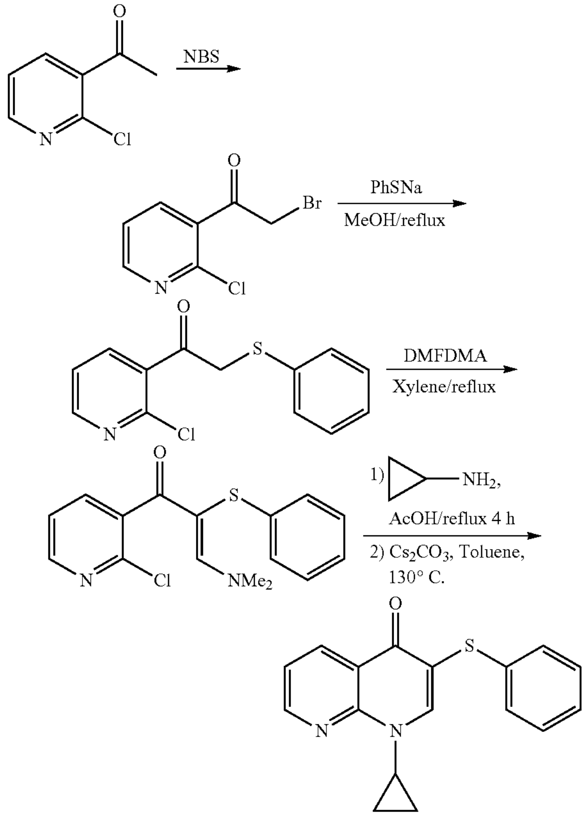

A specific method for the preparation of compound I24 was the same as Example 6, except that NBS (N-bromosuccinimide) was used as a brominating reagent in the reaction of step (1) to prepare a relevant bromo intermediate, and sodium thiophenolate was used instead of sodium benzenesulfinate in step (2). Analytical data for target compound I24 MS (ESI) m/z 295.4 $(M+H)^+$, calcd. for $C_{17}H_{14}N_2OS$ m/z=294.1.

EXAMPLE 8

This example of the present application provides a polysubstituted nitrogen-containing heterocyclic derivative, the specific structure of which is shown in compound I27 of Table 1, and the preparation reaction formula thereof is:

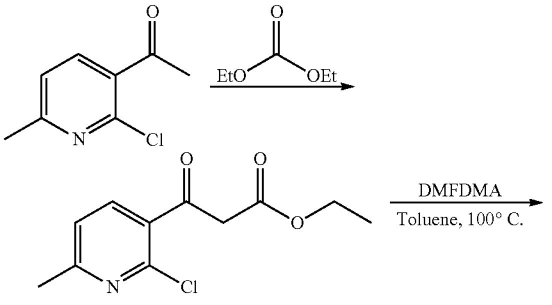

-continued

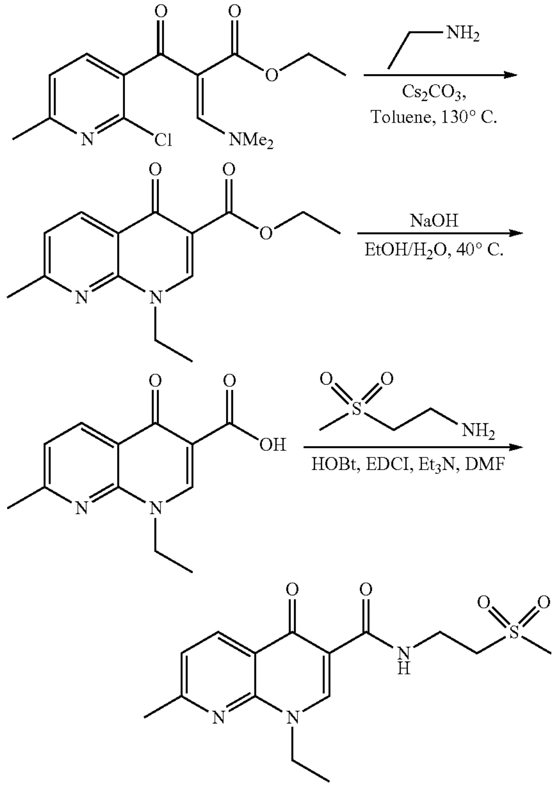

A specific method for the preparation of compound I27 included: steps (1) to (4) were referred to the method of Example 2. (5) In a 50 mL round-bottomed flask, the intermediate 1-ethyl-7-methyl-4-oxo-1,4-dihydro-1,8-naphthyridine-3-carboxylic acid (1 mmol, 1 eq), HOBt (1.5 mmol, 1.5 eq), EDCI (1.5 mmol, 1.5 eq) and DMF (6 mL) were successively added, and the mixture was stirred to be completely dissolved; methylsulfonylethylamine hydrochloride (1 mmol, 1 eq) was then added, followed by slow dropwise addition of $Et_3N$ (3 mmol, 3 eq); the mixture was stirred for reaction at room temperature overnight; the reaction solution was poured into a beaker containing 30 mL of ice water to precipitate a solid; the solid was filtered by suction and washed with a small amount of water to obtain a crude grey solid. Analytical data for target compound I27: MS (ESI) m/z 338.2 $(M+H)^+$, calcd. for $C_{15}H_{19}N_3O_4S$ m/z=337.1.

EXAMPLE 9

This example of the present application provides a polysubstituted nitrogen-containing heterocyclic derivative, the specific structure of which is shown in compound I29 of Table 1, and the preparation reaction formula thereof is:

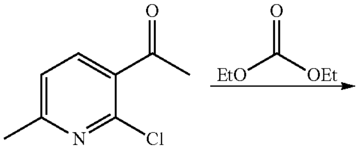

-continued

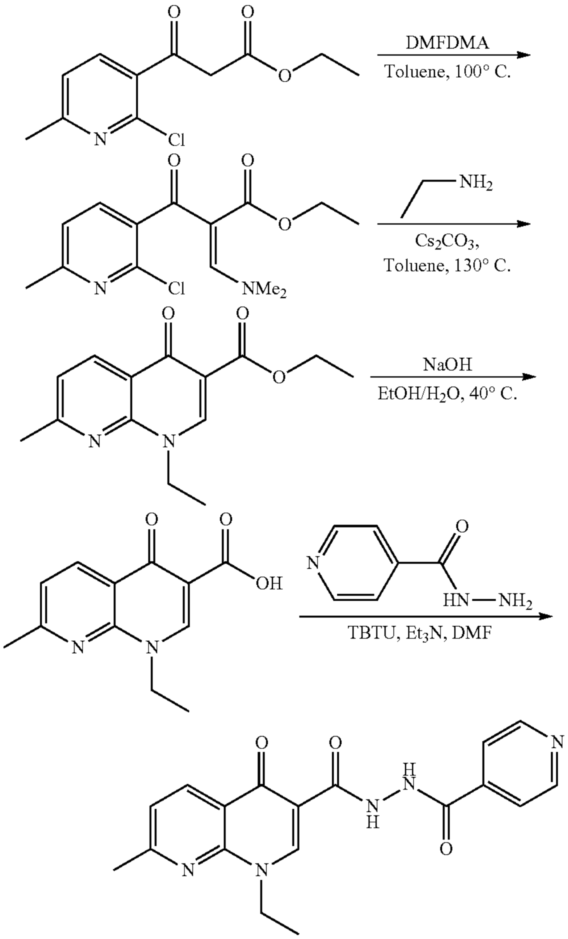

A specific method for the preparation of compound I29 included: steps (1) to (4) were referred to the method of Example 2. (5) A 50 mL round-bottomed flask was charged with the intermediate 1-ethyl-7-methyl-4-oxo-1,4-dihydro-1,8-naphthyridine-3-carboxylic acid (1 mmol, 1 eq) and TBTU (1.5 mmol, 1.5 eq); 10 mL of DMF was added and stirred to be dissolved completely; $Et_3N$ (4 mmol, 4 eq) was added dropwise, and the mixture was stirred for reaction for 1 h; then isonicotinic acid hydrazide (1 mmol, 1 eq) was added, and the mixture was stirred for reaction at room temperature; the reaction was monitored by TLC until the reaction was completed; the reaction solution was cooled to room temperature, added with 50 ml of water, and stirred; the reaction product was extracted with DCM, washed with saturated brine, washed with water, dried, and rotary-evaporated to give the crude product; the crude product was purified by column chromatography on silica gel to give a pure compound. Analytical data for target compound I29: MS (ESI) m/z 352.4 $(M+H)^+$, calcd. for $C_{18}H_{17}N_5O_3$ m/z=351.1.

EXAMPLE 10

This example of the present provides a polysubstituted nitrogen-containing heterocyclic derivative, the specific structure of which is shown in compound I40 of Table 1, and the preparation reaction formula thereof is:

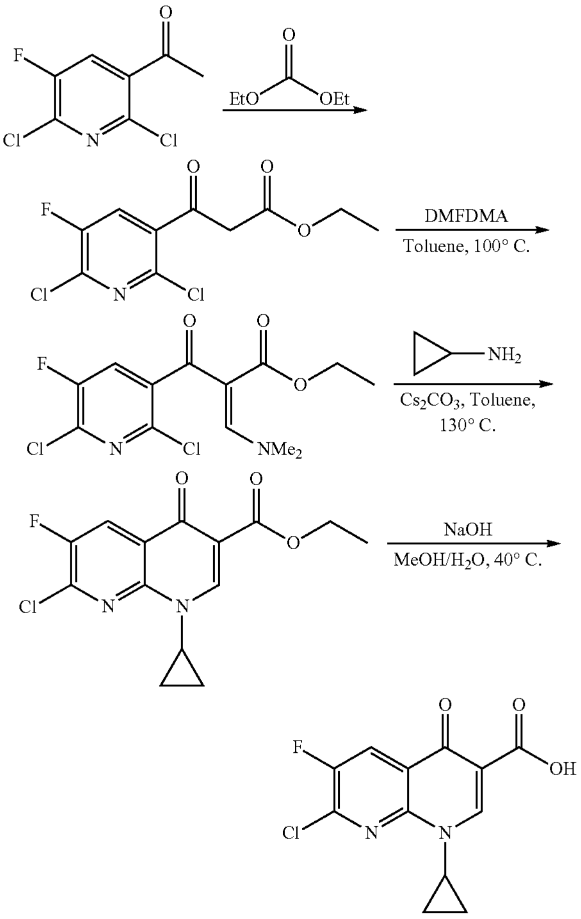

A specific method for the preparation of compound I40 included: with reference to the method of Example 2, only the conditions of different substrates, solvents, and reaction temperatures were appropriately replaced according to the test conditions. Analytical data for target compound I40: MS (ESI) m/z 283.2 $(M+H)^+$, calcd. for $C_{12}H_8ClFN_2O_3$ m/z=282.0.

EXAMPLE 11

This example of the present application provides a polysubstituted nitrogen-containing heterocyclic derivative, the specific structure of which is shown in compound I41 of Table 1, and the preparation reaction formula thereof is:

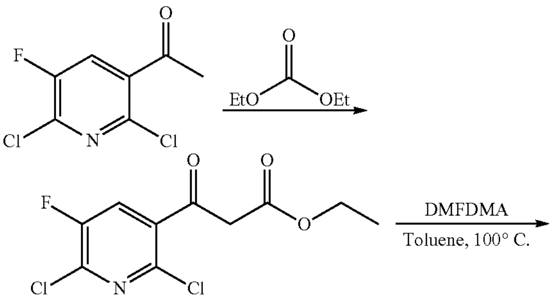

-continued

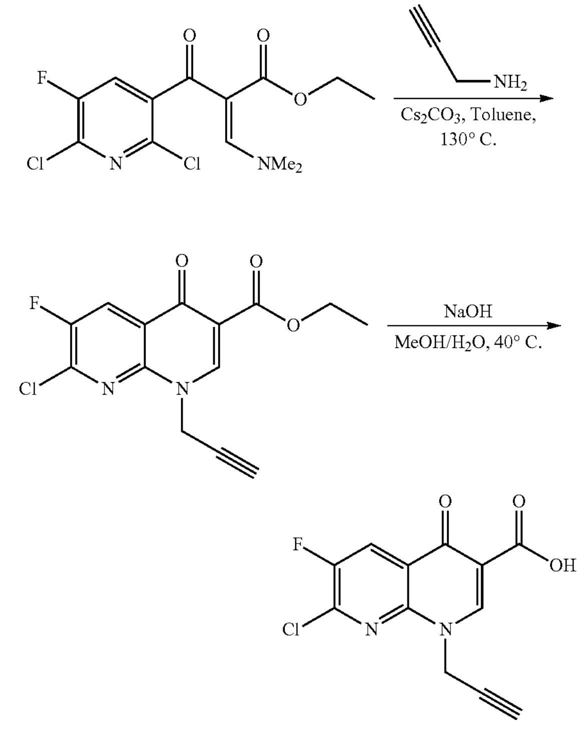

A specific method for the preparation of compound I41 included: with reference to the method of Example 2, only the conditions of different substrates, solvents, and reaction temperatures were appropriately replaced according to the test conditions. Analytical data for target compound I41: MS (ESI) m/z 281.2 $(M+H)^+$, calcd. for $C_{12}H_6ClFN_2O_3$ m/z=280.0.

EXAMPLE 12

This example of the present application provides a polysubstituted nitrogen-containing heterocyclic derivative, the specific structure of which is shown in compound I42 of Table 1, and the preparation reaction formula thereof is:

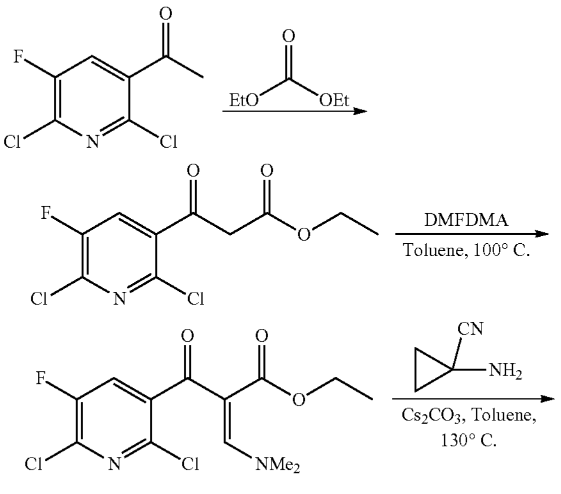

-continued

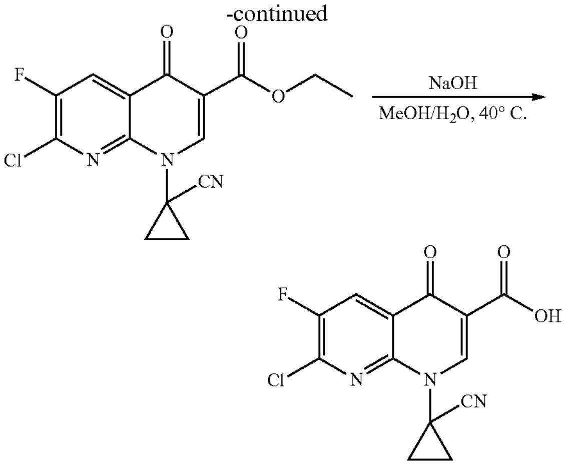

A specific method for the preparation of compound I42 included: with reference to the method of Example 2, only the conditions of different substrates, solvents and reaction temperatures were appropriately replaced according to the test conditions. Analytical data for target compound I42: MS (ESI) m/z 308.4 $(M+H)^+$, calcd. for $C_{13}H_7ClFN_3O_3$ m/z=307.0.

For the preparation of other compounds in Table 1, by referring to the basic synthetic method described in Examples 2-12 above and combining the structural characteristics of the compounds mentioned in Table 1, different chemical raw materials can be selected to prepare other compounds listed in the table.

Bactericidal Activity Test

The nitrogen-containing heterocyclic compound of Example 1 was selected for preliminary screening for bactericidal activity, the test target was *R. solanacearum,* and the test method used was the Oxford cup method. Specifically, the sterilized agar medium was heated to be completely melted, poured into a Petri dish, 15 ml per dish (lower layer), and allowed to be solidified. In addition, the thawed PDA medium was cooled to about 50° C., and mixed with the test bacteria. 5 ml of the medium mixed with the bacteria was added to the solidified medium to be solidified (upper layer). Through the aseptic operations, the Oxford cup was placed vertically on the surface of the culture medium and gently pressed to contact with the culture medium without a gap. The sample to be tested was added to the cup. At the end of the addition, the medium was incubated at 37° C. for 16-18 hours with the front side up. The results were observed, and the zone of inhibition can reflect the activity of the compound.

FIG. 1 shows the preliminary screening results for the bactericidal activity of different compounds against *R. solanacearum* (only compounds with a certain activity are listed, and the compound number in the figure corresponds to the compound number in Example 1), and the positive control drugs in the figure are Streptomycin and Bismerthiazol.

As can be seen from FIG. 1, some nitrogen-containing heterocyclic compounds have significant bactericidal activity against *R. solanacearum,* in particular the compounds I2, I36, I38, I40, I42, and I44.

In order to investigate the potential inhibitory activity level and application potential of these compounds against bacterial diseases, the bactericidal spectrum and $LC_{50}$ data of these compounds were determined by the Oxford cup method and turbidimetric method, respectively. The tested targets were *E. coli, E. carotovora,* and *R. solanacearum.*

Firstly, with reference to the test method for the bactericidal activity of *R. solanacearum,* the bactericidal activity of *E. coli* (FIG. 2), *E. carotovora,* and *R. solanacearum* (FIG. 4) at different concentrations was evaluated by the Oxford cup method. The specific evaluation results are shown in FIGS. 2-4 below.

Figure 2:
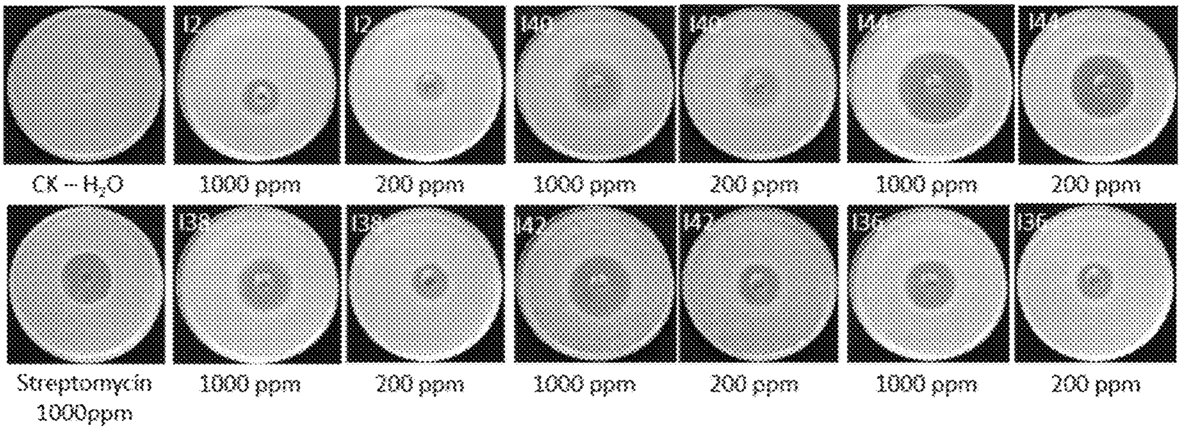
FIG. 2 shows the screening results of bactericidal activity of compounds with different concentrations against *E. coli;*
Figure 3:
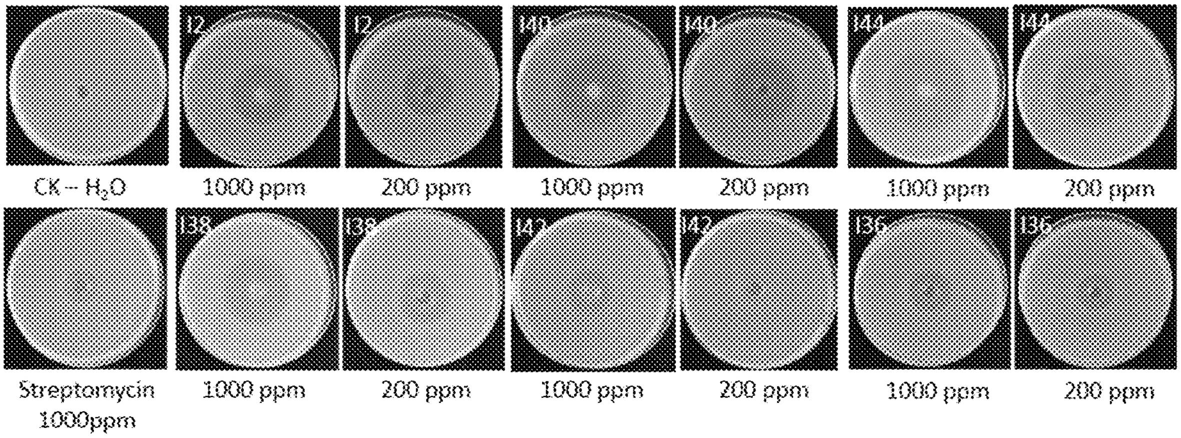
FIG. 3 shows the screening results of the bactericidal activity of compounds with different concentrations against *E. carotovora.
Figure 4:
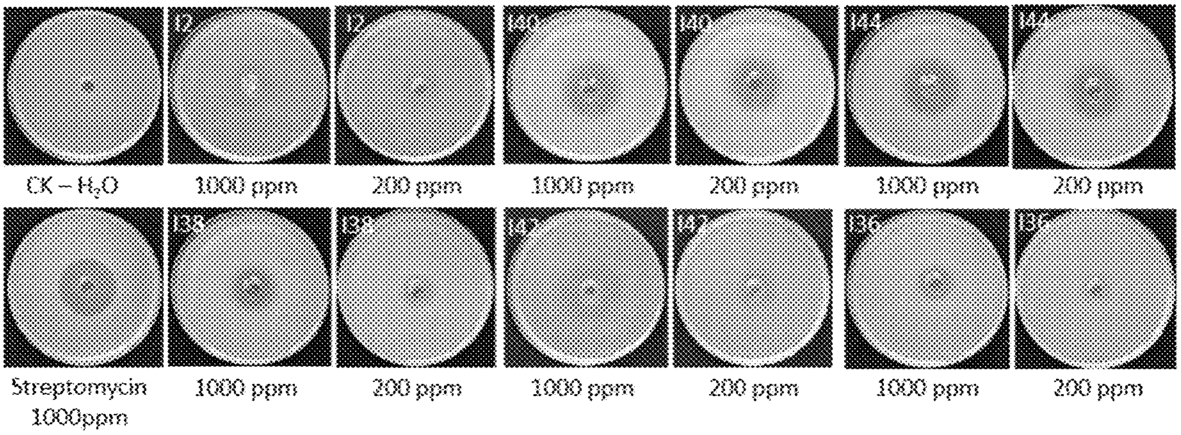
* and FIG. 4 shows the screening results of bactericidal activity of compounds with different concentrations against *R. solanacearum.*

Analysis of the screening results in FIGS. 2-4 shows that the test compound has a significant bactericidal effect on one or more of the tested diseases at the test concentration; especially, some compounds have significantly better bactericidal effects than the control drug Streptomycin at a lower test concentration of 200 ppm.

Subsequently, the turbidimetric method was used to further determine the bactericidal effect of the above-mentioned compounds with high activity. The specific test method was based on the literature [Indoors screening and evaluation of bactericides controlling ginger bacterial wilt]. The medium without liquid medicine was used as the negative control, and the medium without liquid medicine but with bacteria was used as the positive control. The spectrophotometer was used to measure the absorbance value of each liquid medicine treatment group, and the $LC_{50}$ value was calculated using SPSS22.0. The test results for the compounds are shown in Tables 2-4 below (the compound numbers in the table correspond to the compound numbers in Example 1).

TABLE 2

Bactericidal activity of compounds against *E. coli*

| Compound | $LC_{50}$ (ppm) | Linear equation (logx) | $R^2$ |
|---|---|---|---|
| I2 | 0.913 | y = 0.3881x + 0.0149 | 0.9981 |
| I36 | 37.917 | y = 0.5501x − 0.8685 | 0.9984 |
| I38 | 12.643 | y = 2.0585x − 2.287 | 0.9625 |
| I40 | 0.064 | y = 0.2711x + 0.3255 | 0.9898 |
| I42 | 6.162 | y = 0.5485x − 0.4324 | 0.994 |
| I44 | 0.0000091 | y = 0.1153x + 0.5802 | 0.964 |
| Streptomycin | 1.918 | y = 0.6656x − 0.1886 | 0.988 |

TABLE 3

Bactericidal activity of compounds against *E. carotovora*

| Compound | $LC_{50}$ (ppm) | Linear equation (logx) | $R^2$ |
|---|---|---|---|
| I2 | 5.284 | y = 0.4675x − 0.3373 | 0.9805 |
| I36 | 15.743 | y = 0.2355x − 0.282 | 0.9577 |
| I38 | 0.264 | y = 0.2968x + 0.1743 | 0.974 |
| I40 | 4.040 | y = 0.1754x − 0.1063 | 0.9944 |
| I42 | 9.896 | y = 0.2576x − 0.2564 | 0.9941 |
| I44 | 0.00018 | y = 0.0658x + 0.2465 | 0.9764 |
| Streptomycin | 4.519 | y = 1.6374x − 1.0765 | 0.9662 |

TABLE 4

Bactericidal activity of compounds against *R. solanacearum*

| Compound | $LC_{50}$ (ppm) | Linear equation (logx) | $R^2$ |
|---|---|---|---|
| I2 | 13.790 | y = 1.4437x − 1.6452 | 1.000 |
| I36 | 30.519 | y = 1.2828x − 1.901 | 0.9633 |
| I38 | 12.724 | y = 2.0831x − 2.3192 | 0.9547 |
| I40 | 0.002 | y = 0.1808x + 0.6009 | 0.9591 |
| I42 | 34.008 | y = 1.1495x − 1.7593 | 0.9658 |
| I44 | 0.284 | y = 0.3828x + 0.2122 | 0.9689 |
| Streptomycin | 0.169 | y = 0.4388x + 0.3401 | 0.9965 |

The data in Tables 2-4 indicate that the tested compounds I2, I40 and I44 are more active against *E. coli* than the control drugs; the compounds I38, I40, and I44 are more active against *E. carotovora* than the control drugs; the compounds I40 and I44 have significant bactericidal activity against *R. solanacearum.* Through the test results of the Oxford cup and turbidimetric methods mentioned above, it can be determined that these compounds have significant bactericidal activity against bacterial diseases and may become one of the means to solve the resistance of existing bactericides. They can be used as alternative products in production practice and also provide a new technical strategy for the prevention and control of current bacterial diseases.

It can be understood that the bactericides obtained by mixing the polysubstituted nitrogen-containing heterocyclic derivatives of the present application with various adjuvants also have good bactericidal effects on *E. coli, E. carotovora, R. solanacearum,* etc.

The above is only a preferred implementation of the present invention and does not limit it. Any modifications, equivalent substitutions, improvements, etc. made within the spirit and principles of the present invention should be included in the scope of protection of the present invention.

What is claimed is:

1. A method for controlling bacterial diseases in plants, comprising:

applying a polysubstituted nitrogen-containing heterocyclic derivative to plants infected with bacteria;

wherein:

(a) when said bacterial disease is caused by *E. coli*, said polysubstituted nitrogen-containing heterocyclic derivative is

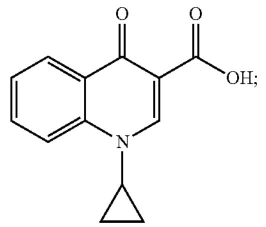 [SMILES: O=C(O)c1cn(C2CC2)c2ccccc2c1=O]

(b) when said bacterial disease is caused by *E. carotovora*, said polysubstituted nitrogen-containing heterocyclic derivative is

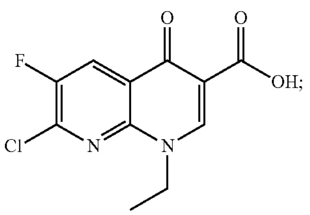 [SMILES: CCn1cc(C(=O)O)c(=O)c2cc(F)c(Cl)nc21]

(c) when said bacterial disease is caused by *R. solanacearum*, said polysubstituted nitrogen-containing heterocyclic derivative is
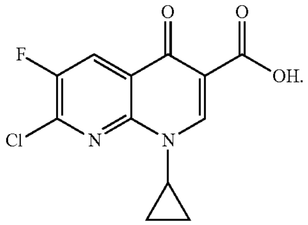 [SMILES: O=C(O)c1cn(C2CC2)c2nc(Cl)c(F)cc2c1=O]
* * * * *